United States Patent [19]

Cheltsov-Bebutov et al.

[11] Patent Number: 4,748,254
[45] Date of Patent: May 31, 1988

[54] MIXED CARBOXYLATO PLATINUM (II) COMPLEXES

[75] Inventors: Petr A. Cheltsov-Bebutov; Alexandr N. Kravchenko; Robert N. Schelokov; Alexandra L. Konovalova; Mikhail A. Presnov; Viktor B. Ivanov, all of Moscow, U.S.S.R.

[73] Assignees: Institut Obschei I Neorganicheskoi Khimii Imeni N.S. Kurnakova Akademii Nauk SSR; Vsesojuzny Onkologichesky Nauchny Tsentr Akademii Meditsinskikh, both of Moscow, U.S.S.R.

[21] Appl. No.: 779,779
[22] PCT Filed: Jan. 23, 1984
[86] PCT No.: PCT/SU84/00001
§ 371 Date: Sep. 4, 1985
§ 102(e) Date: Sep. 4, 1985
[87] PCT Pub. No.: WO85/03296
PCT Pub. Date: Aug. 1, 1985

[30] Foreign Application Priority Data

Jan. 23, 1984 [WO] PCT Int'l Appl. .................. PCT/SU84/00001

[51] Int. Cl.[4] .............................................. C07F 15/00
[52] U.S. Cl. ..................... 549/206; 556/40; 556/137
[58] Field of Search ................... 549/206; 556/40, 137

[56] References Cited

U.S. PATENT DOCUMENTS 4,115,418 9/1978 Gale et al. ............................ 556/137
4,140,707 2/1979 Cleare et al. ...................... 556/17 X
4,225,529 9/1980 Hydes et al. ......................... 556/137
4,329,299 5/1982 Hydes .................................. 556/137
4,614,811 9/1986 Gandolfi ............................. 556/137

FOREIGN PATENT DOCUMENTS 41644 12/1981 European Pat. Off. .
2406440 5/1979 France .
34983 2/1985 Japan .
2140804 12/1984 United Kingdom .

*Primary Examiner*—Richard L. Raymond
*Attorney, Agent, or Firm*—Burgess, Ryan & Wayne

[57] ABSTRACT

Novel platinum(II) carboxylatocomplexes of the following general formula:

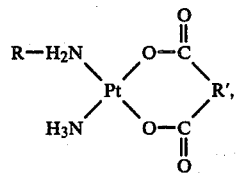

wherein R is tetrahydrofurfuryl or cyclo-$C_nR''_{2n-1}$, R'' is H, an alkyl, hydroxyl, n=3-6; R' is —$CH_2$—, —$CH_2$—$CH_2$—, —CH(OH)—, —CH(OH)—$CH_2$—, —CH(OH)—CH(OH)—.

These compounds possess a clearly pronounced antitumor activity and are readily soluble in water.

A process for preparing these compounds comprises reacting K [$PtCl_3NH_3$] with KI, followed by treatment of the reaction mixture with tetrahydrofurfurylamine or an alicyclic amine and treatment of the resulting mixture of complexes with a silver salt of the formula: $Ag_2$(OOC—R'—COO), wherein R' is as identified above.

4 Claims, No Drawings

MIXED CARBOXYLATO PLATINUM (II) COMPLEXES

FIELD OF THE INVENTION

The present invention relates to complex platinum compounds and, more specifically, to mixed carboxylate platinum(II) complexes and to a process for preparing same.

Mixed carboxylate platinum complexes are biologically active compounds which exhibit antitumor activity.

BACKGROUND OF THE INVENTION

Known in the art is a complex platinum compound, viz. cis-dichlorodiamine platinum(II) (DDP) (Nature; vol. 222, 1969 (Macmillan (Journals) LTD, London) B. Rosenberg, L. Van Camp, J. E. Trosko, V. H. Mansour: "Platinum Compounds; A New Class of Antitumor Agents", p. 385).

This platinum compound has the formula:

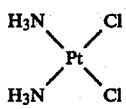

and reveals a high antitumor activity.

It possesses a remarkably wide spectrum of action on diverse tumors, activity in respect of rapidly growing and slowly developing neoplasms, as well as activity in respect of not only early-formed (small-size) neoplasms but also in respect of well-formed and even far-gone and disseminated neoplasms; it is also characterized by the absence of typical specificity.

Nevertheless, likewise all antitumor compounds, in addition to the effect on neoplasms, DDP exhibits a toxic effect the organism, thus limiting dosage of this compound and frequently forcing discontinuation of the treatment due to a toxic effect of the compound on kidney. The $LD_{50}$ of this platinum complex (the dose at which 50% of the test animals are dead) is the same for mice and rats—about 13 mg/kg (Vestnik AMN SSSR, No. 2, 1979 (Medicina, Moscow); M. A. Presnov, A. L. Konovalova, V. P. Koral'chuk "Complex Compounds of Platinum in Chemotherapy of Malignant Tumors", p. 72).

Furthermore, an insufficient solubility of DDP in water (0.25 mass % at 25° C.) complicates the use of this preparation in clinics and makes it impossible to carry out a local treatment of the tumor with a solution containing a high concentration of the preparation.

Also known in the art are platinum(II) dichlorocomplexes with two molecules of primary alicyclic amines, beginning with cyclopropylamine and ending with cyclooctylamine also revealing antitumor properties and corresponding to the formula:

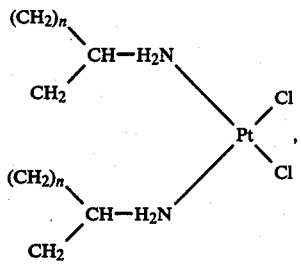

wherein n is 1 to 6 (Chem.-Biol. Interaction, vol. 5, 1972, Elsevier, Netherlands): T. A. Connors, M. Jones, W. C. J. Ross, P. D. Braddock, A. R. Khokhar, M. L. Tobe "New platinum complexes with antitumor activity", see p. 421–422). Chem.-Biol. Interaction, vol. 11, 1975 (Elsevier, Netherlands): P. D. Braddock, T. A. Connors, M. Jones, A. R. Khokhar, D. H. Melzack, M. L. Tobe "Structure and activity relationships of platinum complexes with antitumor activity", p. 153).

On regrafted plasmacytoma of mice ADJ/PC6A these complexes show a high antitumor activity, the highest selectivity of their action is observed for complexes with cyclopentyl- and cyclohexylamine (therapeutical indexes (TI/equal to the ratio of the $LD_{50}$ to the inhibiting dose (ID) suppressing growth of the tumor by 90%, $TI = LD_{50}/ID_{90}$ are equal to 200 and above 267 respectively). These very high therapeutical index values have caused clinical tests of cis-[PtCl$_2$(cyclo-C$_5$H$_9$NH$_2$)$_2$] (cf. Cancer Treatment Reports, vol. 63, No. 9–10, September-October 1979 (national Cancer Institute, Bethesda); J. M. Hill, E. Loeb, A. Pardue, A. Khan, J. J. King, C. Aleman, N. O. Hill "Platinum Analogs of Clinical Interest", see p. 1510, 1512).

This compound, however, is substantially insoluble in water, wherefore it should be administered in the form of fine suspensions in sesame oil or in the form of aqueous solloids stabilized by polyvinylpyrrolidone. The administration of the compound in these forms has shown that it substantially remains at the spot of the injection and no therapeutic response or a side effect, apart from a local irritation upon administration of an oily suspension, is observed, wherefore further tests were stopped.

Known in the art is also a mixed chloride platinum(II) complex containing ammonia and cyclopentylamine having formula: cis-[PtCl$_2$NH$_3$(cyclo-C$_5$H$_9$NH$_2$)] (cf. British Pat. No. 2,060,615A Cl. C 07 F 15/00, A 61 K 31/555 published in 1981).

Tests of the compound on a regrafted plasmacytoma of mice ADJ/PC6A have shown that the compound is slightly more toxic than DDP ($LD_{50}$ are 11.0 and 13.0 mg/kg respectively), but it inhibits growth of tumors by 90% in a dose which is by 3 times as less as that of DDP and nearly 5 times as less as that of cis-[PtCl$_2$(cyclo-C$_5$H$_9$NH$_2$)$_2$]/ID$_{90}$ is equal to 0.5, 1.6 and 2.4 mg/kg respectively).

However, in the paper (Cancer Treatment Reports, vol. 63, No. 9–10, September-October, 1979 (National Cancer Institute, Bethesda): T. A. Connors, M. J. Cleare, K. R. Harrap "Structure-Activity Relationships of the Antitumor Platinum Coordination Complexes", see p. 1501) a conclusion is made to the effect of absence of advantages of this mixed complex as compared to the parent compounds with identical ligands.

As regards solubility in a 0.9% NaCl (about 1 mg/ml), the mixed platinum complex does not differ from DDP (see J. E. Schurig, W. T. Bradner, J. B. Huftalen, G. J. Doyle, J. A. Gylys "Toxic side effects of platinum analogs" in: A. W. Prestyako, S. T. Crooke (Eds.) Cisplatin Current Status and New Developments", 1980, Academic Press (New York), see p. 228, 230).

For the synthesis of this mixed complex of platinum a known method of synthesis of such compounds has been used which is based on interaction of the complex K [PtCl$_3$(NH$_3$)] with cyclopentylamine. The yield of the purified product is 4.8% (see the British Patent referred to hereinabove).

DISCLOSURE OF THE INVENTION

The present invention is directed to the provision of novel mixed platinum(II) carboxylate complexes which would possess an antitumor activity and would be soluble in water, as well as to the provision of a process for preparing same.

This object has been accomplished by the provision of novel mixed platinum(II) carboxylato complexes which, according to the present invention have the general formula:

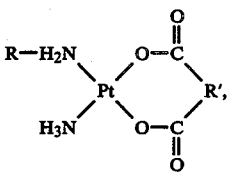

wherein R is tetrahydrofurfuryl or cyclo-C$_n$R''$_{2n-1}$, wherein R'' is H, an alkyl, a hydroxyl, n=3 to 6, R' is —CH$_2$—, —CH$_2$—CH$_2$—, —CH(OH)—, —CH(OH)—CH$_2$—, —CH(OH)—CH(OH)—.

The compounds according to the present invention possess a considerable antitumor activity on a number of graft strains of tumors and leukoses of mice which is reflected in inhibition of tumor growth and in a considerable extension of the life span of animals with leukoses. The compounds according to the present invention have an advantage residing in their high solubility in water, a higher antitumor activity and a lower toxicity as compared to cis-dichloroammine platinum.

The process for preparing the mixed carboxylato platinum(II) complexes according to the present invention consists in the following steps:

(1) interaction of potassium trichloroammineplatinate(II) of the formula K[PtCl$_3$NH$_3$] with potassium iodide in an aqueous medium in a molar ratio of 1:4-6;

(2) treatment of the resulting reaction mixture with an amine such as tetrahydrofurfurylamine or an amine of the formula: cyclo-C$_n$R''$_{2n-1}$—NH$_2$, wherein n=3 to 6, R'' is H, an alkyl, a hydroxyl, to give a mixture of platinum complexes cis-[PtClNH$_3$A] and cis-[PtI$_2$NH$_3$A], wherein A is the above-mentioned amine;

(3) interaction of the resulting mixture of platinum complexes with a silver salt of a dicarboxylic acid of the formula: Ag$_2$(OOC—R'—COO), wherein R' is —CH$_2$—, —CH$_2$—CH$_2$—, —CH(OH)—, —CH(OH)—CH$_2$—, —CH(OH)—CH(OH)— in an aqueous medium.

The reaction of the components in the stage (1, 2) can be carried out at room temperature, while the reaction of the components in stage (3) should be preferably carried out at a mild heating to the temperature of 45° C.

The reaction of the components in stage (3) should be better conducted at a molar ratio equal or close to the stoichiometric one. This results in the preparation of a product of a higher purity grade.

The process according to the present invention can be readily implemented on a commercial scale, since it is simple and requires no high rates of energy consumption.

From the above-given formula it is seen that in the compounds according to the present invention as neutral ligands ammonia and tetrahydrofurfurylamine or an alicyclic amine beginning with cyclopropylamine (n=3) and ending with cyclohexylamine (n=6) are used which are connected to platinum through the nitrogen atom and occupying two cis-positions. As the acid bidentate ligand in the compounds of this invention there can be present an anion of malonic acid $^-$OOC—CH$_2$—COO$^-$, or anion of succinic acid $^-$OOC—CH$_2$—CH$_2$—COO$^-$, or anions of their hydroxy derivatives: anion of hydroxymalonic (tartronic) acid $^-$OOC—CH(OH)—COO$^-$ acid, malic acid $^-$OOC—CH$_2$—CH(OH)—COO$^-$ or tartaric acid $^-$OOC—CH(OH)—CH(OH)—COO$^-$. The compounds with the moiety of malic acid can exist in the form of two geometric isomers differing in the position of hydroxy group relative to two different amines (structures /a/ and /b/)

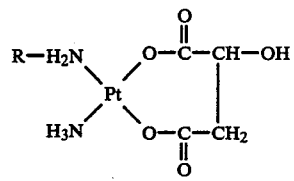

(a)

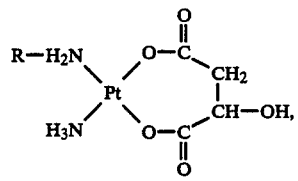

(b)

wherein R has the meaning as in the general formula hereinabove.

Almost equal amounts of these isomers are formed in the syntheses. For the synthesis of complexes with anions of acids containing chiral centers (malic acid, tartaric acid) both optically active naturally-occurring forms of these acids (S(—)-malic acid and R,R(+)-tartaric acid) and racemic acids, as well as meso-form of tartaric acid can be used.

The location of neutral ligands in all of the complexes in the cis-position relative to one another follows from the procedure of their synthesis and is justified by the bidentatic coordination of moieties of dicarboxylic acids forming six- or seven-membered cycles. Chelate cycles of this size can terminate only cis-positions in the complex. The bidentate coordination of moieties of dicarboxylic acids in the compounds is proven by the presence, in their IR-spectra, of bands corresponding to oscillations of deprotonized coordinated groups —COO$^-$ (in the region of 1,600 cm$^{-1}$).

The compounds according to the present invention comprise fine-crystal powders of white or greyish-white powder extremely well soluble in water, a physiological solution of NaCl, in aqueous solutions of glucose (solubility of the complexes is above 200 mg per ml). This high solubility in water is unusual for non-electrolyte complexes of platinum(II) containing no acid groups readily substituted with water or side fragments ionized in solution which represent a valuable property of the compounds according to the present invention. The compounds are stable in storage in dark places at a temperature within the range of from $+5°$ to $0°$ C. (in a refrigerator).

The compounds according to the present invention can be exemplified by: malonatoammine(cyclopropylamine)platinum(II), malonatoammine(cyclobutylamine)platinum(II), (hydroxymalonato)ammine(cyclobutylamine)platinum(II), malonatoammine(cyclopentylamine)platinum(II), (hydroxymalonato)ammine(cyclopentylamine)platinum(II), S(−)malatoammine(cyclopentylamine)platinum(II), RS-malatoammine(cyclopentylamine)platinum(II), R,R(+)-tartratoammine(cyclopentylamine)platinum(II), racem-tartratoammine(cyclopentylamine)platinum(II), meso-tar-tratoammine(cyclopentylamine)platinum(II), succinatoammine(cyclopentylamine)platinum(II), malonatoammine(cyclohexylamine)platinum(II), (hydroxymalonato)ammine(cyclohexylamine)platinum(II), S(−)-malatoammine(cyclohexylamine)platinum(II), succinatoammine(cyclohexylamine)platinum(II), S(−)-malatoammine(2-methylcyclohexylamine)platinum(II), S(−)-malatoammine(3-methylcyclohexylamine)platinum(II), S(−)-malatoammine(4-methylcyclohexylamine)platinum(II), S(−)-malatoammine (4-hydroxycyclohexylamine)platinum(II), malonatoammine(tetrahydrofurfurylamine)platinum(II), S(−)-malatoammine(tetrahydrofurfurylamine)platinum(II).

The synthesis of the compounds by the process according to the present invention can be represented by the following scheme:

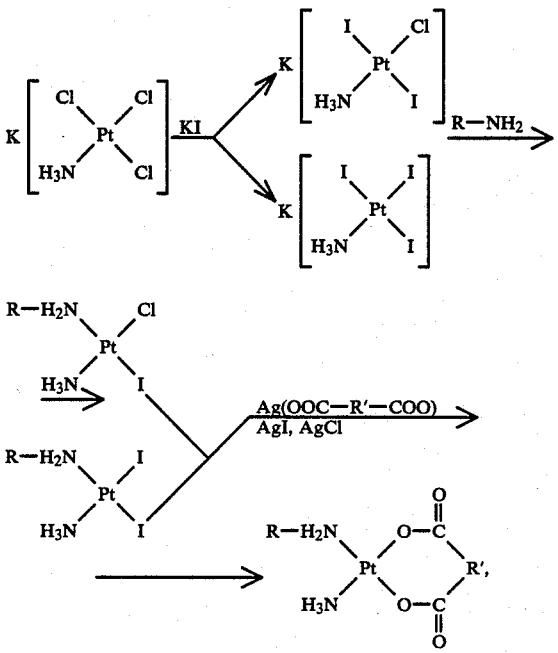

wherein R is tetrahydrofurfuryl or cyclo-$C_nR''_{2n-1}$, where $R''$ is H, an alkyl, hydroxy, n=3–6, R' is —$CH_2$, —$CH_2$—$CH_2$—, —$CH(OH)$—, —$CH(OH)$—$CH_2$—, —$CH(OH)$—$CH(OH)$—.

In the first stage of the synthesis potassium trichloroammineplatinate(II) $K[PtCl_3NH_3]$ is reacted in an aqueous medium with potassium iodide in a molar ratio of 1:(4–6).

Then the resulting reaction mixture is treated with the above-specified amine to yield a yellow-brown mixture of diiodo- and iodochlorocomplexes cis-$[PtI_2NH_3\cdot(R—NH_2)]$ and cis-$[PtClINH_3(R—NH_2)]$ in a yield of 75–90%. At a molar ratio of $K[PtCl_3NH_3]$:KI above or below the above-specified value in the stage (I) the intermediate mixture of diiodo- and iodo-chlorocomplexes obtained in the stage (2) becomes strongly contaminated with by-products. The resulting mixture of complexes is reacted with the above-mentioned silver salt.

On completion of the reaction the mixture of AgCl and AgI is separated by filtration, the filtrate is thickened by evaporation in vacuum and the desired compound is precipitated by an alcohol, acetone or any other suitable organic solvent. The process according to the present invention makes it possible to produce the desired compounds with a sufficient purity and a good yield (up to 70% as calculated for the starting $K[PtCl_3NH_3]$).

All the reactants employed in the process according to the present invention are well known substances which are readily available.

BEST MODE FOR CARRYING OUT THE INVENTION

The highest antitumor activity among the compounds according to the present invention is exhibited by S(−)-malatoammine(cyclopentylamine)platinum(II) [Pt(S(−)-OOCCH(OH)CH$_2$COO)NH$_3$(cyclo-C$_5$H$_9$NH$_2$)]·0.5H$_2$O.

This compound is prepared by reacting $K[PtCl_3NH_3]$ with KI in an aqueous medium at the molar ratio of 1:4.5.

Then the resulting reaction mixture is treated with cyclopentylamine to give a mixture of complexes of platinum: cis-[PtI$_2$NH$_3$(cyclo-C$_5$H$_9$NH$_2$)] and cis-[PtClINH$_3$(cyclo-C$_5$H$_9$NH$_2$)]. Then the thus-obtained mixture of platinum complexes is reacted in an aqueous medium with silver S(−)-malate at the molar ratio of 1:1. After separation of the recovered silver halides and thickening of the filtrate in vacuum the final product is isolated by precipitation with acetone.

When used in optimal doses, S(−)-malatoammine(cyclopentylamine)platinum(II) ensures curing of up to 100% of animals with plasmacytoma MOPC-406 and up to 66% of animals with hepatoma 22a; it also provides for the most significant extension of life span of animals with leukemia L-1210 and hemocytoblastosis La (195 and 113% respectively).

For a better understanding of the present invention, some specific examples illustrating preparation of the compounds, their properties and utility are given hereinbelow.

EXAMPLE 1

Preparation of malonatoammine(cyclopropylamine)platinum(II)

[Pt(OOCCH$_2$COO)NH$_3$(cyclo-C$_3$H$_5$NH$_2$)]

To a solution of 9.00 g of K[PtCl$_3$NH$_3$] (25.2 mmol) in 60 ml of water 20.9 g of KI are added (126 mmol; molar ratio 1:5). The solution is kept in darkness for 30 minutes and added under stirring with 1.72 g of cyclopropylamine in 3 ml of water (30.1 mmol; excess 25%). The formed yellow precipitate is filtered-off, washed with a diluted hydrochloric acid and then with water. The compound is dried in darkness in a vacuum-desiccator over P$_2$O$_5$. As a result, a mixture of complexes cis-[PtIClNH$_3$(cyclo-C$_3$H$_5$NH$_2$)] and cis-[PtI$_2$NH$_3$(cyclo-C$_3$H$_5$NH$_2$)] is obtained with the yield of 9.56 g. The content of platinum is 41.3%, the yield for platinum is 80%.

To a suspension of 4.50 g of the resulting mixture of platinum complexes (9.53 mmol) in about 100 ml of water 3.03 g of silver malonate (9.53 mmol) are added. The mixture is stirred in darkness at room temperature for 4 hours till a complete coagulation of silver halides. The precipitate consisting of AgCl and AgI is filtered-off, the filtrate is mixed with activated coal and, after the removal of coal, the filtrate is evaporated in vacuum to a small volume. The compound is isolated by settling from an aqueous solution with ethanol. To recover the compound, it is also possible to use acetone and mixtures of alcohol or acetone with ether purified from peroxides. The recovered white substance is washed with ethanol, dried in a vacuum desiccator at the temperature of 60° C. over P$_2$O$_5$. The product yield is 2.56 g (76% of the theoretical value as calculated for the employed mixture of dihalocomplexes; 60% as calculated for K[PtCl$_3$NH$_3$].

Found, %: Pt 52.3, N 7.5, C 18.5, H 3.6. C$_6$H$_{12}$N$_2$O$_4$Pt. Calculated, %: Pt 52.4, N 7.5, C 19.35, H 3.25.

EXAMPLE 2

Preparation of malonatoammine(cyclobutylamine)platinum(II)

[Pt(OOCCH$_2$COO)NH$_3$(cyclo-C$_4$H$_7$NH$_2$)]

To a solution of 3.52 g of K[PtCl$_3$NH$_3$] (9.84 mmol) in 25 ml of water 8.98 g of KI (54.1 mmol, molar ratio is 1:5.5) are added. The solution is kept in darkness for 25 minutes, added under stirring with 0.77 g of cyclobutylamine in 3 ml of water (10.8 mmol; excess 10%). The formed brownish-yellow precipitate is filtered-off, washed with a diluted hydrochloric acid and then with water. The compound is dried in darkness in a vacuum desiccator over P$_2$O$_5$ to give a mixture of complexes: cis-[Pt-IClNH$_3$(cyclo-C$_4$H$_9$NH$_2$)] and cis-[PtI$_2$NH$_3$(cyclo-C$_4$H$_9$NH$_2$)]. The yield is 3.73 g of the mixture of halocomplexes with the content of platinum of 40.8%, the yield based on platinum is 79%.

To a suspension of 3.64 g of the resulting mixture of complexes (7.62 mmol) in 80 ml 2.42 g of silver malonate (7.62 mmol) are added. The mixture is stirred for 5 hours in darkness at room temperature till a complete coagulation of silver halides. The precipitate consisting of AgCl and AgI is filtered-off, the filtrate is mixed with activated carbon, and after separation of carbon by filtration, evaporated in vacuum to the volume of about 10 ml. The product is separated from the aqueous solution by precipitation with acetone, filtered off, washed with acetone and ether. The resulting white substance is dried in a vacuum desiccator over P$_2$O$_5$. The yield is 2.23 g (76% as calculated for the employed mixture of dihalocomplexes; 60% as calculated for K[PtCl$_3$NH$_3$].

Found, %: Pt 50.8, N 7.3, C 21.5, H 3.8. C$_7$H$_{14}$N$_2$O$_4$Pt. Calculated, %: Pt 50.6, N 7.3, C 21.8, H 3.7.

EXAMPLE 3

Preparation of (hydroxymalonato)ammine(cyclobutylamine)platinum(II)

[Pt(OOCCH(OH)COO)NH$_3$(cyclo-C$_4$H$_7$NH$_2$)]

This complex is prepared in a manner similar to that described for the compound of Example 2 hereinabove. Silver hydroxymalonate is entered into an exchange reaction with a mixture of platinum dihalocomplexes. The compound is isolated from the aqueous solution by precipitation with an alcohol or acetone or by crystallization directly from the concentrated solution upon cooling. The yield is 75% as calculated for the employed mixture of dihalocomplexes; 59% as calculated for K[PtCl$_3$NH$_3$].

Found, %: Pt 48.8, N 6.8, C 21.1, H 3.7. C$_7$H$_{14}$N$_2$O$_5$Pt. Calculated, %: Pt 48.6, N 7.0, C 20.95, H 3.5.

EXAMPLE 4

Preparation of S(−)malatoammine(cyclopentylamine)platinum(II)

[Pt(S(−)-OOCCH(OH)CH$_2$COO)NH$_3$(cyclo-C$_5$H$_9$NH$_2$)]·0.5H$_2$O

To a solution of 8.00 g of K[PtCl$_3$NH$_3$] (22.4 mmol) in about 50 ml of water 16.71 g of KI (100.8 mmol, molar ratio of 1:4.5) are added. The solution is kept in darkness for 20 minutes and added under stirring with 2.29 g (26.9 mmol, excess 20%) of cyclopentylamine in 5 ml of water. The reaction mixture is stirred for 5 minutes. The resulting brownish-yellow precipitate is filtered-off, washed with a diluted hydrochloric acid and water, dried in a vacuum desiccator over P$_2$O$_5$ to give a mixture of cis-[PtIClNH$_3$(cyclo-C$_5$H$_9$NH$_2$)] and cis-[PtI$_2$NH$_3$(cyclo-C$_5$H$_9$NH$_2$)]. The yield of the mixture of these complexes is 9.94 g, the content of platinum is 38.7%, the yield as calculated for platinum is 88%.

To a suspension of 4.50 g of the resulting mixture of dihalocomplexes of platinum (8.93 mmol) in about 100 ml of water 3.11 g of silver S(−)-malate (8.93 mmol) are added. The mixture is stirred in darkness at room temperature for 5 hours to ensure a complete coagulation of silver halides.

After filtering-off the precipitate of silver halides, the filtrate is stirred with activated carbon, the latter is removed by filtration and the filtrate is evaporated in vacuum to the volume of about 10 ml. The compound is settled by addition of acetone, the residue is filtered-off, washed with acetone and dry ether containing no peroxides and immediately afterwards it is placed into a vacuum desiccator to be dried over P$_2$O$_5$.

The compound is hydroscopic, the combined water is not fully removed even after a long-time drying over P$_2$O$_5$. The yield of the dried compound is 2.84 g (72.7% as calculated for the mixture of dihalocomplexes, 64% as clalculated for K[PtCl$_3$NH$_3$].

Found, %: Pt 44.6, N 6.5, C 24.9, H 4.5. C9H19N2O5.5Pt. Calculated, %: Pt 44.5, N 6.4, C 24.7, H 4.4.

EXAMPLE 5

Preparation of RS-malatoammine(cyclopentylamine)platinum(II)

[Pt(RS-OOCCH(OH)CH2COO)NH3(cyclo-C5H9NH2)].0.5H2O

The synthesis of this compound is carried out in a manner similar to that for the compound described in Example 4 hereinabove, except that as the reactant use is made of a silver salt of racemic malic acid.

The subsequent operations are performed according to the procedure of the foregoing Example 4.

The product yield is 49% as calculated for K[PtCl3NH3].

Found, %: Pt 44.3, N 6.2, C 25.1, H 4.7. C9H19N2O5.5Pt. Calculated, %: Pt 44.5, N 6.4, C 24.7, H 4.4.

EXAMPLE 6

Preparation of malonatoammine(cyclopentylamine)platinum(II)

[Pt(OOCCH2COO)NH3(cyclo-C5H9NH2)]

The preparation of this complex is effected in a manner similar to that described for the synthesis of the compound of Example 4 hereinabefore. 2.52 g of silver malonate (7.93 mmol) are entered into an exchange reaction with 4.00 g of mixture of dihalocomplexes cis-[PtI2NH3(cyclo-C5H9NH2)] and cis-[PtIClNH3(cyclo-C5H9NH2)] (7.93 mmol) in 70 ml of water. The mixture is stirred in darkness upon heating to the temperature of 45° C. for 4 hours till a complete coagulation of silver halides. The filtrate after separation of silver halides is mixed with activated carbon, the latter is separated by filtration, the filtrate is evaporated in vacuum till the formation of a viscous solution, the residual water is removed by a three-time evaporation in vacuum with absolute ethanol and the compound is precipitated by the addition of acetone. The formed white precipitate is washed with acetone and dry ether containing no peroxides. The substance is immediately placed into a vacuum desiccator and dried over P2O5, since the wet substance is very hygroscopic. The yield of the dried substance is 2.49 g (81% as calculated for the employed mixture of dihalocomplexes; 71% as calculated for K[PtCl3NH3]).

Found, %: Pt 49.0, N 7.3, C 23.9, H 4.1. C8H16N2O4Pt. Calculated, %: Pt 48.7, N 7.0, C 24.0, H 4.0.

EXAMPLE 7

Preparation of (hydroxymalonato)ammine(cyclopentylamine)-platinum(II)

[Pt(OOCCH(OH)COONH3(cyclo-C5H9NH2)]

The preparation of this compound is carried out in a manner similar to the synthesis of the compound described in Example 4 hereinbefore. Silver hydroxymalonate is entered into an exchange reaction with a mixture of platinum dihalocomplexes. After separation of silver dihalides and treatment of the reaction mixture with activated carbon the compound is isolated from a concentrated aqueous solution by precipitation with acetone and ether.

The product yield is 63% as calculated for K[PtCl3NH3].

Found, %: Pt 47.2, N 6.6, C 23.0, H 3.6. C8H16N2O5Pt. Calculated, %: Pt 47.0, N 6.8, C 23.1, H 3.9.

EXAMPLE 8

Preparation of R,R(+)-tartratoammine(cyclopentylamine)platinum-(II)

[Pt(R,R(+)-OOCCH(OH)CH(OH)COO)NH3(cyclo-C5H9NH2)].H2O

The preparation of this compound is conducted in a manner similar to the synthesis of the compound described in Example 4. Into an exchange reaction with a mixture of platinum dihalocomplexes silver R,R(+)-tartrate is entered.

The product yield is 57% as calculated for K[PtCl3NH3].

Found, %: Pt 41.8, N 6.0, C 23.6, H 4.5. C9H20N2O7Pt. Calculated, %: Pt 42.1, N 6.1, C 23.3, H 4.4.

EXAMPLE 9

Preparation of racem.-tartratoammine(cyclopentylamine)platinum(II)

[Pt(racem.-OOCCH(OH)CH(OH)COO)NH3(cyclo-C5H9NH2)].H2O

The preparation of this compound is carried out in a manner similar to the synthesis of the compound described in Example 4 hereinbefore. A silver salt of racemic tartaric acid is entered into an exchange reaction with a mixture of platinum dihalocomplexes. The product yield is 52% as calculated for K[PtCl3NH3].

Found, %: Pt 41.7, N 6.0, C 23.7, H 4.6. C9H20N2O7Pt. Calculated, %: Pt 42.1, N 6.1, C 23.3, H 4.4.

EXAMPLE 10

Preparation of meso-tartratoammine(cyclopentylamine)platinum(II)

[Pt(meso-OOCCH(OH)CH(OH)COO)NH3(cyclo-C5H9NH2)].H2O

The preparation of this compound is carried out in a manner similar to the synthesis of the compound described in Example 4. A silver salt of meso-tartaric acid is entered into a reaction of exchange with a mixture of platinum dihalocomplexes.

The product yield is 61% as calculated for K[PtCl3NH3].

Found, %: Pt 41.9, N 6.1, C 23.5, H 4.7. C9H20O7Pt. Calculated, %: Pt 42.1, N 6.1, C 23.3, H 4.4.

EXAMPLE 11

Preparation of succinatoammine(cyclopentylamine)platinum(II)

[Pt(OOCCH2CH2COO)NH3(cyclo-C5H9NH2)]

The preparation of this compound is carried out in a manner similar to the synthesis of the compound described in Example 4 hereinbefore. Silver succinate is entered into an exchange reaction with a mixture of platinum dihalocomplexes.

The product yield is 69% as calculated for K[PtCl$_3$NH$_3$].

Found, %: Pt 47.0, N 6.6, C 26.4, H 4.5. C$_9$H$_{18}$N$_2$O$_4$Pt. Calculated, %: Pt 47.2, N 6.8, C 26.2, H 4.4.

EXAMPLE 12

Preparation of malonatoammine(cyclohexylamine)platinum(II)

[Pt(OOCCH$_2$COO)NH$_3$(cyclo-C$_6$H$_{11}$NH$_2$)]

To a solution of 3.00 g of K[PtCl$_3$NH$_3$] (8.39 mmol) in 20 ml of water 5.57 g of KI (33.6 mmol, molar ratio 1:4) are added. The solution is kept in darkness for 20 minutes, then added under stirring with 1.16 g (11.7 mmol) of cyclohexylamine in 5 ml of water. The reaction mixture is stirred for 5 minutes. The formed brownish-yellow precipitate is filtered-off, washed with a diluted hydrochloric acid and water, dried in a vacuum desiccator over P$_2$O$_5$. As a result, a mixture of cis-[PtClINH$_3$(cyclo-C$_5$H$_9$NH$_2$)] and cis-[PtI$_2$NH$_3$(cyclo-C$_5$H$_9$NH$_2$)] is obtained. The yield of the mixture is 3.79 g, the content of platinum in this mixture of complexes is 39.7%; the yield as calculated for platinum is 92%.

To a suspension of 3.50 g of the resulting mixture of platinum dihalocomplexes (7.13 mmol) in about 70 ml of water 2.26 g (7.11 mmol) of silver malonate are added. The mixture is stirred in darkness upon heating to the temperature of 40° C. for 7 hours till a complete coagulation of silver halides. After separation of the precipitate of silver halides by filtration the filtrate is mixed with activated carbon, the latter is removed by filtration and the filtrate is evaporated in vacuum till the formation of a viscous solution. The compound is precipitated by the addition of an alcohol and acetone. The resulting white precipitate is washed with acetone, ether and dried in a vacuum desiccator over P$_2$O$_5$.

The product yield is 2.21 g (75% as calculated for the mixture of dihalocomplexes, 69% as calculated for K[PtCl$_3$NH$_3$].

Found, %: Pt 47.2, N 6.6, C 26.3, H 4.4. C$_9$H$_{18}$N$_2$O$_4$Pt. Calculated, %: Pt 47.2, N 6.8, C 26.2, H 4.4.

EXAMPLE 13

Preparation of (hydroxymalonato)ammine(cyclohexylamine)platinum(II)

[Pt(OOCCH(OH)COO)NH$_3$(cyclo-C$_6$H$_{11}$NH$_2$)]

The preparation of this compound and isolation thereof are carried out in a manner similar to that described in the foregoing Example 12. Silver hydroxymalonate is entered into an exchange reaction with a mixture of dihalocomplexes.

The product yield is 64% as calculated for K[PtCl$_3$NH$_3$].

Found, %: Pt 45.3, N 6.5, C 25.4, H 4.2 C$_9$H$_{18}$N$_2$O$_5$Pt. Calculated, %: Pt 45.4, N 6.5, C 25.2, H 4.2.

EXAMPLE 14

Preparation of S(−)malatoammine(cyclohexylamine)platinum(II)

[Pt(S(−)-OOCCH(OH)CH$_2$COO)NH$_3$(cyclo-C$_6$H$_{11}$NH$_2$)].H$_2$O

The preparation of this compound and isolation thereof are carried out in a manner similar to that described in Example 12 hereinbefore. Silver S(−)-malate is entered into an exchange reaction with a mixture of dihalocomplexes.

The product yield is 59% as calculated for K[PtCl$_3$NH$_3$].

Found, %: Pt 42.0, N 6.1, C 26.2, H 5.0. C$_{10}$H$_{22}$N$_2$O$_6$Pt. Calculated, %: Pt 42.3, N 6.1, C 26.0, H 4.8.

EXAMPLE 15

Preparation of succinatoammine(cyclohexylamine)platinum(II)

[Pt(OOCCH$_2$CH$_2$COO)NH$_3$(cyclo-C$_6$H$_{11}$NH$_2$)]

The preparation of this compound is carried out in a manner similar to the synthesis of the compound described in Example 12 hereinbefore. Into an exchange reaction with a mixture of dihalocomplexes silver succinate is entered.

The product yield is 69% as calculated for K[PtCl$_3$NH$_3$].

Found, %: Pt 45.5, N 6.7, C 28.0, H 4.9. C$_{10}$H$_{20}$N$_2$O$_4$Pt. Calculated, %: Pt 45.7, N 6.6, C 28.1, H 4.7.

EXAMPLE 16

Preparation of S(−)-malatoammine(2-methylcyclohexylamine)platinum(II)

[Pt(S(−)-OOCCH(OH)CH$_2$COO)NH$_3$(2-CH$_3$-cyclo-C$_6$H$_{10}$NH$_2$)].0.5H$_2$O To a solution of 4.00 g of K[PtCl$_3$NH$_3$] (11.7 mmol) in about 25 ml of water 8.36 g of KI (50.4 mmol, molar ratio of 1:4.5) are added. The solution is kept in darkness for 20 minutes and added under stirring with 1.52 g of 2-methylcyclohexylamine (13.4 mmol) in 5 ml of water. The reaction mixture is stirred for 5 minutes. The resulting brownish-yellow precipitate is filtered-off, washed with a diluted hydrochloric acid and water, dried in a vacuum desiccator over P$_2$O$_5$ to give a mixture of cis-[PtClINH$_3$(2-CH$_3$-cyclo-C$_6$H$_{10}$NH$_2$)] and cis-[PtI$_2$NH$_3$(2-CH$_3$-cyclo-C$_6$H$_{10}$NH$_2$)]. The yield of the mixture of these complexes is 5.28g; the content of platinum is 36.7% the yield as calculated for platinum is 89%.

The exchange reaction of the resulting mixture of platinum dihalocomplexes with silver S(−)-malate and recovery of the final product are carried out as described in Example 4 hereinbefore.

The yield of the final product is 3.34 g (64% as calculated for K[PtCl$_3$NH$_3$].

Found, %: Pt 41.9, N 6.0, C 28.5, H 5.1. C$_{11}$H$_{23}$N$_2$O$_{5.5}$Pt. Calculated, %: Pt 41.8, N 6.0, C 28.3, H 5.0.

EXAMPLE 17

Preparation of S(−)malatoammine(3-methyl-cyclohexylamine)platinum(II)

[Pt(S(−)-OOCCH(OH)CH$_2$COO)NH$_3$(3-CH$_3$-cyclo-C$_6$H$_{10}$NH$_2$)].0.5H$_2$O The synthesis of this compound is effected in a manner similar to that described for the compound of Example 16. As the reactant for the preparation of a mixture of platinum dihalocomplexes 3-methylcyclohexylamine is used.

The final product is obtained in the yield of 61% as calculated for K[PtCl$_3$NH$_3$].

Found, %: Pt 42.0, N 6.1, C 28.0, H 5.2. C$_{11}$H$_{23}$N$_2$O$_{5.5}$Pt. Calculated, %: Pt 41.8, N 6.0, C 28.3, H 5.0.

EXAMPLE 18

Preparation of
S(—)-malatoammine(4-methylcyclohexylamine)-platinum(II)

[Pt(S(—)-OOCCH(OH)CH$_2$COO)NH$_3$(4-CH$_3$-cyclo-C$_6$H$_{10}$NH$_2$)].0.5H$_2$O The synthesis of this compound is carried out in a manner similar to that for the compound according to Example 16. As the reactant for the preparation of a mixture of platinum dihalocomplexes 4-methylcyclohexylamine is used.

The final product is obtained in the yield of 65% as calculated for K[PtCl$_3$NH$_3$].

Found, %: Pt 42.1, N 5.9, C 27.9, H 5.1. C$_{11}$H$_{23}$N$_2$O$_{5.5}$Pt. Calculated, %: Pt 41.8, N 6.0, C 28.3, H 5.0.

EXAMPLE 19

Preparation of
S(—)-malatoammine(4-hydroxycyclohexylamine)-platinum(II)

[Pt(S(—)-OOCCH(OH)CH$_2$COO)NH$_3$(4-OH-cyclo-C$_6$H$_{10}$NH$_2$)]. H$_2$O

The synthesis of this compound is carried out in a manner similar to that for the compound described in Example 16 hereinbefore. As the reactant for the preparation of a mixture of platinum dihalocomplexes 4-hydroxycyclohexylamine is used.

The final product is obtained in the yield of 58% as calculated for K[PtCl$_3$NH$_3$].

Found, %: Pt 40.6, N 5.8, C 25.4, H 4.7. C$_{10}$H$_{22}$N$_2$O$_7$Pt. Calculated, %: Pt 40.9, N 5.9, C 25.2, H 4.6.

EXAMPLE 20

Preparation of
malonatoammine(tetrahydrofurfurylamine)platinum(II)

[Pt(OOCCH$_2$COO)NH$_3$(C$_4$H$_7$OCH$_2$NH$_2$)]

To a solution of 4.00 g of K[PtCl$_3$NH$_3$] (11.2 mmol) in about 25 ml of water 8.36 g of KI (50.4 mmol, molar ratio of 1:4.5) are added. The solution is kept in darkness for 20 minutes and added under stirring with 1.36 g of tetrahydrofurfurylamine (13.4 mmol) in 5 ml of water. The reaction mixture is stirred for 5 minutes. The resulting yellow residue is filtered-off, washed with a diluted hydrochloric acid and water dried in a vacuum desiccator over P$_2$O$_5$ to give a mixture of cis-[PtClINH$_3$(C$_4$H$_7$OCH$_2$NH$_2$)] and cis-[PtI$_2$NH$_3$(C$_4$H$_7$OCH$_2$NH$_2$)].

The yield of the mixture of these complexes is 4.91 g; the content of platinum is 40.7%, the yield as calculated for platinum is 91.5%.

To 4.60 g of the mixture of these platinum complexes (9.60 mmol) suspended in about 70 ml of water 3.05 g of silver malonate (9.60 mmol) are added. The reaction mixture is stirred in darkness upon heating to the temperature of 40° C. for 6 hours. The precipitated mixture of AgCl and AgI is filtered-off. The filtrate is intermixed with activated carbon. After separation of the latter by filtration the filtrate is evaporated in vacuum and the final product is precipitated by the addition of ethanol and acetone. The precipitated substance is washed with dry ether and dried in a vacuum desiccator over P$_2$O$_5$. The product yield is 3.16 g or 68% as calculated for K[PtCl$_3$NH$_3$].

Found, %: Pt 46.6, N 6.6, C 23.4, H 4.0. C$_8$H$_{16}$N$_2$O$_5$Pt. Calculated, %: Pt 47.0, N 6.8, C 23.1, H 3.9.

EXAMPLE 21

Preparation of
S(—)-malatoammine(tetrahydrofurfurylamine)-platinum(II)

[Pt(S(—)-OOCH(OH)CH$_2$COO)NH$_3$(C$_4$H$_7$OCH$_2$NH$_2$)].H$_2$O

The synthesis of this compound is carried out in a manner similar to that of the compound described in the foregoing Example 20. Silver S(—)-malate is entered into an exchange reaction with a mixture of platinum dihalocomplexes. The final product is obtained in the yield of 59% as calculated for K[PtCl$_3$NH$_3$].

Found, %: Pt 41.6, N 5.9, C 23.9, H 4.1. C$_9$H$_{10}$N$_2$O$_7$Pt. Calculated, %: Pt 42.1, N 6.0, C 23.3, H 4.4.

The antitumor activity of the compounds according to the present invention has been studied on a number of strains of grafted solid tumors and leukosises of mice: plasmacytoma MOPC-406, lymphoid leukosis L-1210, hemocytoblastosis La, hepatoma 22a, mammal adenocarcinoma Ca 755.

As the criteria for the antitumor activity for leukosises and ascytic forms of tumors the increase of the lifespan of treated animals (ILS, %)

$$ILS\% = T - C/C \cdot 100,$$

wherein:
T—average lifespan of treated animals;
C—average lifespan of control animals;
and for a solid tumor—tumor growth inhibition (TGI, %)

$$TGI5 = O - K/K \cdot 100,$$

wherein:
O—volume of tumors in the group of treated animals;
K—volume of tumors in the control group were employed.

The experiments were carried out on line mice and their hybrides of the first generation. For the purpose of comparison, simultaneously studied was the antitumor activity of cis-dichlorodiammineplatinum(II) (DDP). The compounds were administered to animals intraperitoneally in a 5% solution of glucose once or daily over 5 days within the time limits adopted in experimental studies of corresponding tumors. DDP was administered in the same manner in a 0.9% solution of NaCl. The results obtained in these comparative experiments are represent in Table 1 hereinbelow.

TABLE 1

Antitumor activity of mixed platinum carboxylatocomplexes (II)

| No. | Compound | Optimal dose range, mg/kg | Days of treatment | Increase of lifespan, % Hepatoma 22a | L-1210 | La | MOPC-406 | Tumor growth inhibition, % Ca-755 |
|---|---|---|---|---|---|---|---|---|
| 1 | 2 | 3 | 4 | 5 | 6 | 7 | 8 | 9 |
| 1. | Malonatoammine(cyclopropylamine)platinum(II) of Example 1 | 60–70 | 2 | — | 48 | — | 177(1/6) | |
| | | 60 | 7 | — | — | — | 150(1/6) | |
| | | 15–25 | 2–6 | 85(0/6) | 39 | 29 | 268(2/6) | 89 |
| 2. | (Hydroxymalonato)ammine(cyclobutylamine)platinum(II) of Example 3 | 60 | 2 | — | 71 | — | — | — |
| | | 25 | 2–6 | — | 100 | — | — | |
| | | 20 | 2–6 | — | — | — | — | 70 |
| 3. | Malonatoammine(cyclopentylamine)platinum(II) of Example 6 | 40–60 | 2 | — | 45 | — | 300(5/6) | |
| | | 50 | 7 | — | — | — | 329(3/6) | |
| | | 15–25 | 2–6 | 140(2/6) | 36 | 21 | 286(3/6) | 76 |
| 4. | S(−)-Malatoammine(cyclopentylamine)platinum(II) of Example 4 | 60–80 | 2 | — | 101 | — | 310(5/6) | |
| | | 20 | 7–11 | — | — | — | 356(3/6) | |
| | | 15–25 | 2–6 | 225(4/6) | 195 | 113 | 327(6/6) | 96 |
| 5. | RS—Malatoammine(cyclopentylamine)platinum(II) of Example 5 | 20–25 | 2–6 | 322(2/6) | 156 | — | 350(4/6) | 95 |
| 6. | Succinatoammine(cyclohexylamine)platinum(II) of Example 15 | 150 | 2 | — | 120 | — | — | |
| | | 30 | 2–6 | — | 108 | — | — | 72 |
| 7. | S(−)-Malatoammine(tetrahydrofurfurylamine)platinum(II) of Example 21 | 20–40 | 2–6 | 340(2/6) | 120 | — | 280(3/6) | 95 |
| 8. | Cis-Dichlorodiammineplatinum(II)/ prior art compound (DDP)/ | 3 | 1–5 | — | 116 | — | — | |
| | | 8 | 1 | — | — | 200 | — | |
| | | 2 | 2–5 | — | — | — | 140(0/6) | |
| | | 5 | 3 | 120(0/6) | — | — | — | |
| | | 8 | 2 | — | — | — | — | 95 |

Note:
Shown in brackets is the number of cured animals divided by the number of animals employed for the experiment. Symbol (—) defines that no experiment was carried out.

As it follows from the Table, all the compounds according to the present invention exhibit a strong antitumor effect. The latter is revealed in a considerable increase of the lifespan of mice with leukosis L-1210, MOPG-406, hepatoma 22a and in a strong inhibition of growth of a solid tumor adenocarcinoma Ca-755. Furthermore, the compound of Example 4 considerably extends the lifespan of animals with hemocytoblastosis La. It should be noted that compounds of Examples 1, 4, 6, 5, 21 ensure curing of a certain number of animals (up to 100%) in the case of plasmocytoma MOPC-406, while compounds of Examples 4, 6, 5, 21 cure a portion of animals with hepatoma 22a. In experiments with DDP no curing of animals with these tumors is observed. Maximum tolerable doses of all the complexes tested are considerably higher as compared to DDP which points to their lower molar toxicity. The maximum tolerable doses of a single-time administration are within the range of from 50 to 150 mg/kg (for DDP-8 mg/kg), for a 5-days' treatment course-20–40 mg/kg (for DDP-3 mg/kg).

Therefore, the compounds according to the present invention feature a high antitumor activity and have their specific characteristics of the antitumor effect.

It should be also noted that an important advantage of the compounds according to the present invention is their high solubility in water and aqueous solution employed for injections, whereas the majority of known platinum complexes revealing an antitumor activity are sparingly soluble or substantially insoluble in water.

INDUSTRIAL APPLICABILITY OF THE INVENTION

The mixed platinum carboxylatocomplexes according to the present invention can be useful in pharmaceutical industry for the preparation, on their basis, of pharmaceutical compositions employed in medicine for the treatment of malignant tumors and leukosises.

We claim:

1. Platinum(II) carboxylatocomplexes of the formula:

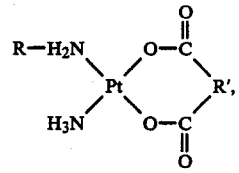

wherein R is tetrahydrofurfuryl or a cyclo-$C_nR''_{2n-1}$, each $R''$ is independently H, an alkyl, or hydroxyl, $n=3-6$, $R'$ is —$CH_2$—, —$CH_2$—$CH_2$—, $CH(OH)$—, —$CH(OH)$—$CH_2$—, or —$CH(OH)$—$CH(OH)$—.

2. A platinum(II) carboxylatocomplex according to claim 1, characterized in that in the general formula R is cyclo-$C_5H_9$ and $R'$ is —$CH(OH)$—$CH_2$—.

3. A platinum(II) carboxylatocomplex according to claim 1, characterized in that in the formula R is

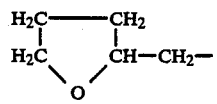

and $R'$ is —$CH(OH)$—$CH_2$—.

4. A platinum(II) carboxylatocomplex according to claim 1, characterized in that in the formula R is cyclo-$C_5H_9$ and $R'$ is —$CH_2$—.

* * * * *